United States Patent
Roeher

(10) Patent No.: US 6,579,241 B2
(45) Date of Patent: Jun. 17, 2003

(54) DIALYSIS APPARATUS USING A BLOOD PRESSURE METER AND A CONTROLLER

(75) Inventor: Otfried Roeher, Dresden (DE)

(73) Assignee: B. Braun Melsungen Medizintechnologie GmbH, Melsungen (DE)

( * ) Notice: Subject to any disclaimer, the term of this patent is extended or adjusted under 35 U.S.C. 154(b) by 0 days.

(21) Appl. No.: 10/053,599

(22) Filed: Jan. 24, 2002

(65) Prior Publication Data

US 2002/0107449 A1 Aug. 8, 2002

(30) Foreign Application Priority Data

Jan. 24, 2001 (DE) .......................... 101 03 048

(51) Int. Cl.⁷ ................................ A61B 5/02
(52) U.S. Cl. ................ 600/485; 600/481; 210/646; 210/741; 604/67
(58) Field of Search .................. 600/481, 483, 600/485, 490, 492, 493, 494, 495, 496, 497; 210/646, 439, 741; 604/67

(56) References Cited

U.S. PATENT DOCUMENTS

| 4,710,164 A | * | 12/1987 | Levin et al. ............ 604/66 |
| 6,406,434 B2 | * | 6/2002 | Inukai et al. .......... 600/490 |
| 6,423,022 B1 | * | 7/2002 | Roeher et al. ......... 604/5.01 |

* cited by examiner

Primary Examiner—Max F. Hindenburg
Assistant Examiner—Navin Natnithithadha
(74) Attorney, Agent, or Firm—Diller, Ramik & Wight

(57) ABSTRACT

In a dialysis apparatus the blood pressure is normally monitored at intervals of 5 minutes. According to the invention the current blood pressure curve (33) is measured only during the first 45 minutes at intervals of 5 minutes and then compared with the stored blood pressure curves of previous treatments of the same patient. On the basis of statistical analyses that blood pressure curve is determined from a data storage, which shows the largest similarity to the current blood pressure curve and used as the basic curve (35) for blood pressure control during the current treatment. During further treatment the blood pressure measurement is carried out at intervals from 15 minutes to 30 minutes. This considerably reduces the number of blood pressure measurements and the resultant discomfort of the patient.

6 Claims, 3 Drawing Sheets

DIALYSIS APPARATUS USING A BLOOD PRESSURE METER AND A CONTROLLER

BACKGROUND OF THE INVENTION

The present invention relates to a therapy means comprising a blood pressure meter and a controller, and in particular to a therapy means for extracorporeal blood cleaning.

In various therapies, such as the hemodialysis, it is necessary to continuously monitor the patient's blood pressure. For this purpose means for non-invasive blood pressure measurement are used, said means comprising a cuff which is placed around the patient's arm, inflated and then slowly deflated with the blood pressure being measured. During this process the systolic and diastolic blood pressures are measured. To realize a quasi-continuous blood pressure measurement, measurements must be performed at intervals of a few minutes. In automatic blood pressure meters the cuff inflates automatically. During a therapy of several hours thus frequent repetitions of the described measuring process are required.

SUMMARY OF THE INVENTION

It is an object of the present invention to configure a therapy means, where blood pressure measurement at intervals is required, such that the number of measuring processes is reduced.

According to the present invention the blood pressure measurement is left undone at some of the times provided for this purpose and the measured values are substituted by hypothetical values gathered from a former blood pressure curve determined during a therapy undergone by the same patient.

Clinical experience with regard to dialysis patients have shown that the blood pressure curves of the patients lie within patient-specific scatter ranges during the dialysis treatment despite the intraindividual variabilty. If, after a first treatment period of e.g. 45 minutes, the current blood pressure curve is subjected to a statistical comparison with the stored curves determined during previous treatments of the same patient, a previous curve can be used as a basic curve whose values can be assumed as the actual blood pressure values. Thus a large portion of the presently required blood pressure measurements may become superfluous. In an initial phase the current blood pressure curve can be measured at short intervals of e.g. 5 minutes and compared with the stored blood pressure curves determined during previous treatments of the same patient. On the basis of statistical analyses and the relevant treatment parameters the previous blood pressure curve, which shows the largest similiarity to the current blood pressure curve, is determined from data storage and used as a basic curve for blood pressure control during the current treatment.

The present invention actively incorporates patient-specific experience regarding the blood pressure behaviour during previous treatments into the optimization of the current treatment. Depending on the course of the treatment the basic-curve method allows approximately 60% of the previously necessary blood pressure measurements taken on the patient to be omitted. The memory-based method does not require any additional measuring means or instruments. The required computation and memory capacities are small.

Preferably the controller, which controls, inter alia, the blood pressure measurement, carries out the following steps:

a) preparing and storing a collection of the time histories of the blood pressure determined during a plurality of therapy sessions to generate stored blood pressure curves and, b) carrying out successive blood pressure measurements during a therapy session to obtain a current blood pressure curve, c) determining, from the stored curves, as the basic curve a blood pressure curve which shows the largest similarity to the current blood pressure curve, d) controlling the blood pressure utilizing values of the basic curve for the actual blood pressure value.

According to a preferred aspect of the present invention it is provided that subsequent to the utilization of values of the basic curve another measurement of the blood pressure is carried out, and the new measured value is used as the actual blood pressure value for control purposes. After the new measurement the previous blood pressure curve can be checked for similarity to the stored blood pressure curves to select a new basic curve, if necessary. Thus the statistical analysis can be repeated after each blood pressure measurement to select the optimum basic curve for the respective treatment phase.

According to a preferred aspect of the present invention it is provided that the extent of similarity of the previous blood pressure curve to a stored blood pressure curve decides upon the time interval up to the next measurement. For the similarity measurement statistical method can be used, such as the t test, the pattern-recognition method or the averaging method or combinations thereof. Each of these methods supplies a similarity value which e.g. increases with increasing similarity of the curves compared with each other. The extent of similarity is utilized according to the invention to define the interval between two blood pressure measurements.

The present invention is particularly suitable for dialyzers and other means for extracorporeal blood treatment, but also e.g. for the infusion therapy.

BRIEF DESCRIPTION OF THE DRAWINGS

Hereunder an embodiment of the present invention is explained in detail with reference to the drawings in which.

DESCRIPTION OF THE PREFERRED EMBODIMENT

Figure 1:
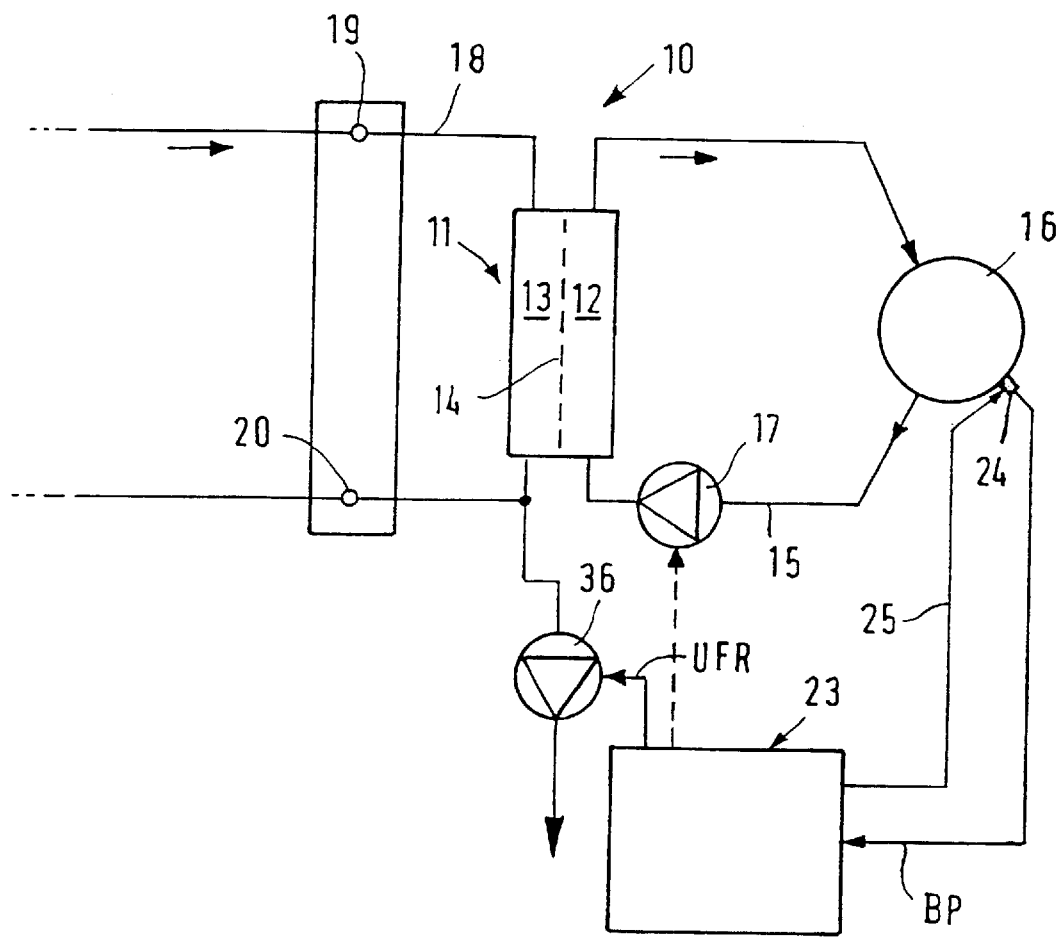
FIG. 1 shows a schematic representation of a dialyzer.

The basic setup of the dialyzer shown in FIG. 1 corresponds to that described in EP 0 956 872 A2. The dialyzer 10 comprises an ultrafiltration device 11 having a primary chamber 12 and a secondary chamber 13 separated from each other by a membrane 14. The primary chamber 12 forms part of a blood circulation 15 where blood, which has been taken off via the arterial system from the patient's body, is cleaned in the ultrafiltration device 11 and then returned via the venous system to the patient's body 16. A pump 17 is arranged in the blood circulation 15. This pump is configured as a volumetric pump, i.e. the pumping capacity of this pump corresponds to the drive velocity and is controllable.

The secondary chamber 13 of the ultrafiltration device 11 is located in a hemodialysis solution path 18 in which hemodialysis solution is pumped. The hemodialysis solution is supplied from a storage tank (not shown), takes up additional substances from the blood in the ultrafiltration device 11 and is then pumped to a discharge (not shown). In the hemodialysis solution path a flow chamber 19 and 20, respectively, is located upstream and downstream of the secondary chamber 13, which flow chambers control the flow rate at the respective location. The flow chamber 19 and the flow chamber 20 have the same flow rate. Via the volume-controlled ultrafiltration pump 36 the desired ultrafiltration quantity UFV is drawn off at a fixed ultrafiltration rate. The time integral across the ultrafiltration rate UFR forms the ultrafiltration volume UFV, i.e. that solution volume which has passed through the membrane 14 as from the beginning of the treatment. The ultrafiltration rate is controlled by a controller 23 which supplies control signals for the pumping rate of the pump 36. The pumping rate of the pump is adjusted such that it results in a desired ultrafiltration rate.

The controller 23 further receives the blood pressure signal BP of a blood pressure meter 24 fastened to the patient's body. The blood pressure meter comprises an inflatable cuff which is placed around the patient's upper arm, and carries out non-invasive blood pressure measurements at intervals. Control of the intervals is effected by the controller 23 via lines 25. Besides the blood pressure value BP blood pressure trend values can also be supplied to the controller, as described in EP 0 956 872 A2. The controller 23 controls the ultrafiltration rate UFR as a function of the input variables fed to the controller 23.

Figure 2:
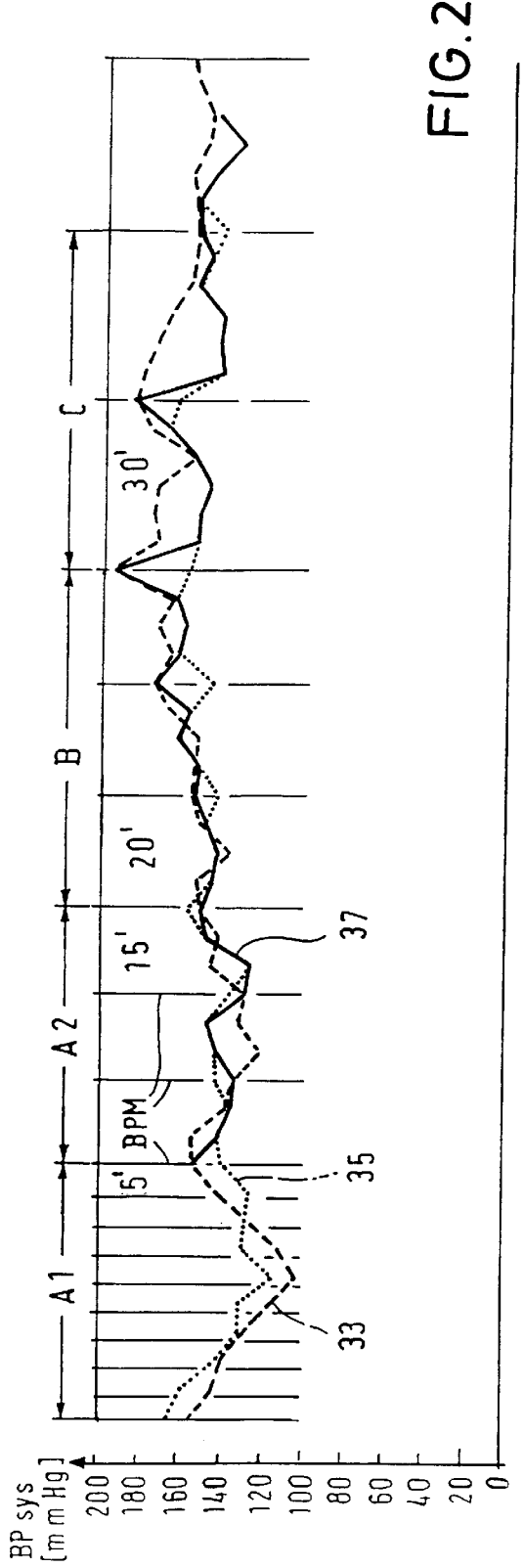
FIG. 2 shows a time diagram of the dialysis treatment with representation of the ultrafiltration rate and the blood pressure.
Figure 2:
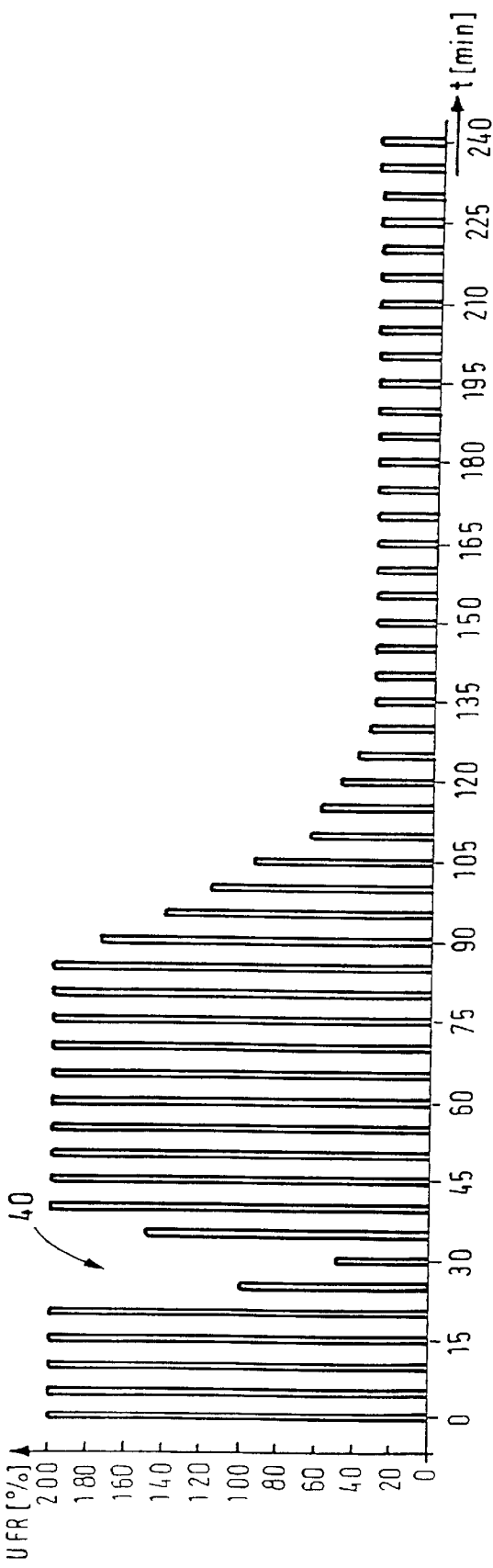

FIG. 2 shows in the lower half an example of the time history of the relative ultrafiltration rate UFR (in %). In a dialysis treatment a high relative ultrafiltration rate of 200% is employed first and then the ultrafiltration rate is decreased to a minimum value of approximately 35%.

In the upper half of FIG. 2 the systolic blood pressure BPsys of a patient during a dialysis treatment is plotted. The dashed line shows the current blood pressure curve 33 which would result from a continuous blood pressure measurement.

In the controller 23 or in a central computer a collection of the time histories of the blood pressure determined during previous therapy sessions is stored.

In an initial phase A1 the current blood pressure is measured with the blood pressure meter 24 at intervals of 5 minutes and stored as blood pressure curve 33. The blood pressure is controlled exclusively as a function of the current blood pressure curve 33. In the present embodiment the initial phase A1 takes 45 minutes. At the end of the initial phase A1 the current blood pressure curve 33 is compared with the stored blood pressure curves determined during previous treatments of the same patient. On the basis of statistical analyses (average values, standard deviations, t test or image processing methods) that blood pressure curve is determined from the data storage, which shows the largest similarity to the current blood pressure, and is used as the basic curve 35 (dotted curve) for the current treatment.

In the following second phase A2 blood pressure measurements shown by the dashes BPM are carried out at intervals of 15 minutes. In phase B the blood pressure measurements BPM are carried out at intervals of 20 minutes, and in end phase C in intervals of 30 minutes. However the blood pressure control continues to take place at 5-minute intervals, wherein at times, at which no measurement is carried out, the values of the (dotted) basic curve are taken as a basis as the actual value of the blood pressure, and at times, at which the blood pressure measurement BPM is carried out, the current values of the (dashed) blood pressure curve 33 are taken as a basis as the actual value of the blood pressure. The values used as the actual blood pressure values for control purposes are shown in the continuous curve 37 indicating the "hypothetic blood pressure curve".

FIG. 2 shows that at the times, at which the blood pressure measurement BPM takes place, the hypothetical blood pressure curve, which is important for the control, assumes the value of the current blood pressure 33 (dashed line), whereas in the intervening times the value of the (dotted) basic curve is assumed.

If the actual value decreases to below 120 mmHg, the ultrafiltration rate UFR is reduced, as shown in FIG. 2 in the area 40. By reducing the ultrafiltration rate less fluid is taken off the patient's body, which counteracts a decrease in the blood pressure.

The described procedure ensures that the dynamics of the automatic matching of the ultrafiltration rate UFR and the conductivity of the haemodialysis solution is maintained to a large extent.

Figure 3:
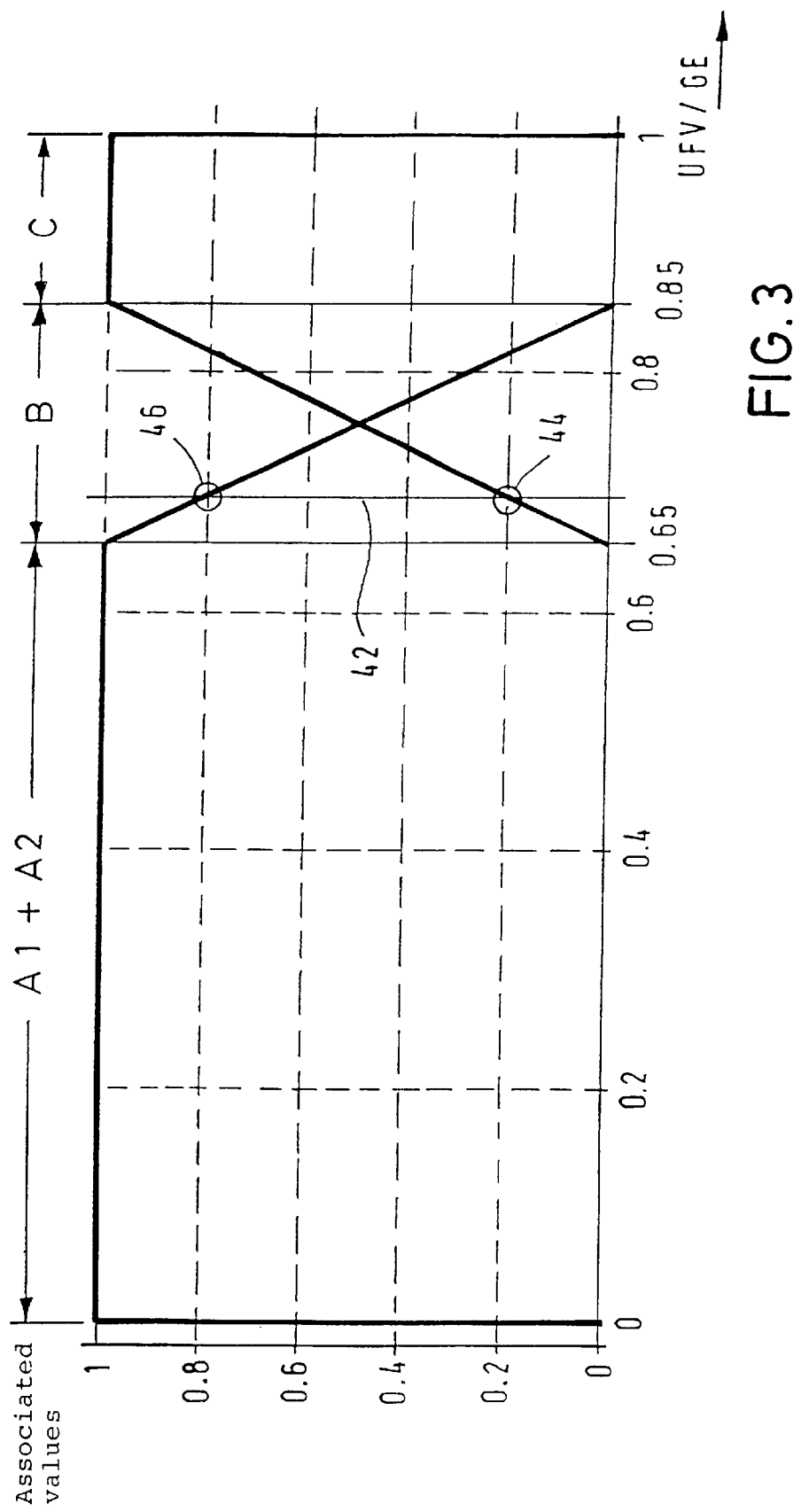
FIG. 3 shows a fuzzy set for the linguistic variable "relative ultrafiltration volume UF/GE".

The overall duration of the treatment is divided into the periods A1, A2, B and C according to the fuzzy set used in the controller. The fuzzy set for the linguistic variable "relative ultrafiltration volume UFV/GE" is shown in FIG. 3. Here, the relative ultrafiltration volume UFV/GE is shown on the abscissa. "UFV" is the measured ultrafiltration volume and "GE" the desired overall withdrawal. On the ordinate the associated values from 0 to 1 are shown. For each value of the current (relative) ultrafiltrate volume a vertical line 42 is produced whose points of intersection with the associated curves result in the respective associated values 44,46 which are processed during fuzzy control.

Although a preferred embodiment of the invention has been specifically illustrated and described herein, it is to be understood that minor variations may be made without departing from the spirit and scope of the invention, as defined in the appended claims.

What is claimed is:

1. Therapy means comprising: a blood pressure meter (24) and a controller (23) for controlling the times of blood pressure measurement and for: determining blood pressure values controlling the blood pressure as a function of the determined blood pressure values, wherein the blood pressure measurement is left undone at some times and the determined blood pressure values are substituted by hypothetical values gathered from a former blood pressure curve determined during a therapy session.

2. Therapy means according to claim 1, wherein the controller (23) carries out the following functions;
   a) preparing and storing a collection of the time histories of the blood pressure determined during a plurality of therapy sessions,
   b) carrying out successive blood pressure measurements during a therapy session to generate stored blood pressure curves and to obtain a current blood pressure curve (33),
   c) determining, from the stored blood pressure curves, as a basic curve (35) a blood pressure curve which shows the largest similarity to the current blood pressure curve (33),
   d) controlling the blood pressure utilizing values of the basic curve (35) for the actual blood pressure value.

3. Therapy means according to claim 1, wherein subsequent to function d) another measurement of the blood pressure is carried out and the new measured value is used as the actual blood pressure value for control purposes.

4. Therapy means according to claim 3, wherein after the new measurement a check of the previous blood pressure curve (33) for similarity to the stored blood pressure curves is carried out.

5. Therapy means according to claim 4, wherein the extent of similarity of the previous blood pressure curve (33) to a stored blood pressure curve decides upon the time interval up to the next measurement.

6. Therapy means according to claim 2, wherein use of the basic curve is inhibited when a lower limit value of the blood pressure is not reached and/or an upper limit value of the blood pressure is exceeded.

* * * * *